US012440376B2

(12) United States Patent
Mcclunan et al.

(10) Patent No.: US 12,440,376 B2
(45) Date of Patent: Oct. 14, 2025

(54) SHUNT AND METHOD FOR TREATING GLAUCOMA

(71) Applicant: LIQID MEDICAL PROPRIETARY LIMITED, Cape Town (ZA)

(72) Inventors: Daemon Bruce Mcclunan, Cape Town (ZA); Joshua David Fischer, Cloetesville (ZA)

(73) Assignee: LIQID MEDICAL PROPRIETARY LIMITED, Cape Town (ZA)

( * ) Notice: Subject to any disclaimer, the term of this patent is extended or adjusted under 35 U.S.C. 154(b) by 0 days.

(21) Appl. No.: 18/772,936

(22) Filed: Jul. 15, 2024

(65) Prior Publication Data

US 2024/0374424 A1 Nov. 14, 2024

Related U.S. Application Data

(63) Continuation of application No. PCT/IB2023/050284, filed on Jan. 12, 2023.

(30) Foreign Application Priority Data

Jan. 14, 2022 (ZA) ................................ 2022/00672

(51) Int. Cl.
*A61F 9/007* (2006.01)

(52) U.S. Cl.
CPC ................................ *A61F 9/00781* (2013.01)

(58) Field of Classification Search
CPC .................................................. A61F 9/00781
See application file for complete search history.

(56) References Cited

U.S. PATENT DOCUMENTS

| | | | |
|---|---|---|---|
| 5,882,327 | A | 3/1999 | Jacob |
| 8,702,639 | B2 | 4/2014 | Van Der Mooren et al. |
| 8,721,656 | B2 | 5/2014 | De Juan, Jr. et al. |
| 9,707,128 | B2 | 7/2017 | Rynerson |
| 11,246,753 | B2 | 2/2022 | Horvath et al. |
| 2024/0285433 | A1 * | 8/2024 | Hamouche .......... A61F 9/00781 |

FOREIGN PATENT DOCUMENTS

WO 2021250609 A1 12/2021

OTHER PUBLICATIONS

International Search Report and Written Opinion of the International Searching Authority for PCT/IB2023/050284 dated Apr. 13, 2023, 8 pages.

* cited by examiner

*Primary Examiner* — Leslie R Deak
(74) *Attorney, Agent, or Firm* — Heslin Rothenberg Farley & Mesiti P.C.

(57) ABSTRACT

A shunt for treating glaucoma comprises a silicone rubber duct for diverting aqueous humor from a chamber of a patient's eye and a fixation body frictionally located on the duct in an arrangement permitting sliding displacement of the fixation body, for fixing and sealing the duct within scleral tissue surrounding the eye. The duct has a rigid proximal portion having a proximal end and a deformable distal portion locatable in the scleral channel and having a distal end. The distal portion is severable, allowing a surgeon to cut the distal portion to a desired length corresponding to the anatomical dimensions of the patient's eye and a required bleb position. The proximal portion has a capillary lumen having a diameter which is smaller than a diameter of a lumen of the distal portion, thereby reducing a flow rate of aqueous humor along the capillary lumen.

33 Claims, 14 Drawing Sheets

SHUNT AND METHOD FOR TREATING GLAUCOMA

CROSS-REFERENCE TO RELATED APPLICATIONS

This application is a bypass continuation of PCT Application No. PCT/IB2023/050284, filed Jan. 12, 2023, and entitled "Shunt and Method for Treating Glaucoma," which claims priority to ZA 2022/00672 filed Jan. 14, 2022, and entitled "Shunt and Method for Treating Glaucoma," which are both incorporated herein by reference in their entirety.

TECHNICAL FIELD

This invention relates to a shunt for treating glaucoma in a patient. The invention relates also to a method for treating glaucoma in a patient. More specifically, the invention relates to a shunt and method for treating glaucoma in a patient by diverting aqueous fluid from a chamber of the eye to the subconjunctival space of the patient.

BACKGROUND OF THE INVENTION

Glaucoma is an ocular disease characterised by the presence of raised intraocular pressure (IOP) causing irreversible damage to the optic nerve. The ocular globe of the eye has a tough outer layer comprised of the sclera and the cornea. The internal areas of the eye are separated into the anterior segment and the posterior segment. The anterior segment comprises the anterior and posterior chambers of the eye filled with aqueous fluid, and the posterior segment comprises the vitreous chamber filled with vitreous gel. The cornea merges into the sclera at a juncture referred to as the limbus. A portion of the sclera is covered by a thin tissue called Tenon's membrane (also called Tenon's capsule), which envelopes the bulb of the eye from the optic nerve to the ciliary region. A portion of the Tenon's membrane is covered by another thin tissue membrane known as the conjunctiva. Near its front, Tenon's membrane blends into the conjunctiva where it is attached to the ciliary region of the eye.

The ocular globe maintains an internal pressure known as the intraocular pressure which normally varies between 10 mmHg and 21 mmHg. The intraocular pressure needs to be controlled within a defined range in order for the eye to function normally. The intraocular pressure is regulated by maintaining a balance between volumes of aqueous fluid produced and drained from the anterior segment of the ocular globe. Aqueous fluid is produced at a rate which varies between 2 to 3 micromillimetres per minute by the ciliary body. Age is one factor which affects the aqueous production rate, with elderly patients having a significantly lower aqueous production rate than younger patients. Aqueous fluid is drained from the anterior chamber through the trabecular and uveoscleral pathways at variable rates. If an impairment occurs in the amount of aqueous fluid drained from the ocular globe, then the intraocular pressure becomes too high. The presence of raised intraocular pressure results in a large pressure differential across the lamina cribrosa (translaminar pressure). This causes damage to the optic nerve head known as glaucoma. Glaucoma causes irreversible visual field defects. These defects enlarge until a patient's field of view is severely restricted. In the end stage of the disease, total vision loss occurs. Glaucoma is a leading cause of blindness worldwide. If the intraocular pressure remains very high, the eye can become persistently painful and may need to be removed.

Current medical, laser and surgical treatment options for glaucoma are aimed at lowering intraocular pressure. Glaucoma which is difficult to control through first line therapies such as topical medications and laser therapy is known as refractory glaucoma. Refractory glaucoma is often managed by glaucoma drainage tube implantation to create an additional aqueous outflow pathway from the anterior chamber into the subconjunctival space. Aqueous fluid draining into the subconjunctival space creates a fluid blister between the sclera and conjunctiva known as a bleb. Over time, the bleb becomes encapsulated by a fibrovascular wall of Tenons tissue.

In the early weeks following implantation, the bleb wall is not well formed and resistance to fluid flowing into the subconjunctival space is minimal. This means that glaucoma drainage devices tend to over drain in the early stages. Due to over drainage in the early stages, the IOP may drop below 5 mmHg. This causes a condition known as hypotony. Hypotony may cause complications such as maculopathy and choroidal effusion.

The resistance to flow into the bleb then gradually increases during bleb wall formation in the intermediate period between 4 and 12 weeks following implantation. It is therefore preferable for devices to provide higher resistance to fluid flow in the early period following implantation to prevent hypotony, and lower resistance to flow in the intermediate to later stages to increase aqueous drainage.

Generally, the size of the bleb relates to the capacity of the bleb to absorb aqueous fluid. In the later stages following device implantation, the size of the bleb may reduce if inflammation and scarring occur due to unhealthy conjunctiva. If the size of the bleb is sufficiently reduced, then filtration failure and the recurrence of glaucoma may occur. In the presence of localised areas of unhealthy conjunctiva, the ideal bleb position for preventing filtration failure may differ between patients. The ideal bleb position may be as close as 4 mm to the limbus or as far posteriorly as 30 mm from the limbus. If the conjunctiva is generally unhealthy, a sub-Tenon's footplate connected to the drainage tube may be required to maintain the surface area of the bleb and help prevent filtration failure.

The presence of a tube in the anterior chamber is known to be a risk for damage to corneal endothelial cells which may result in corneal decompensation, vision loss and eventually a painful condition known as bullous keratopathy. The diameter, length, stiffness, and position of the tube in the anterior chamber are all known to contribute to the risk of endothelial cell damage.

If the tube is not securely fixed to the ocular globe then device migration may occur. Device migration may result in the tube becoming dislodged from within the anterior chamber or damage to endothelial cells.

Traditional aqueous drainage devices such as the Baerveldt device (U.S. Pat. No. 6,050,970) consist of a continuous diameter silicone tube with an outer diameter of about 0.6 mm and internal diameter of about 0.3 mm attached to a large footplate. The footplate is sutured to the sclera in the subconjunctival space at a position 10 mm behind the limbus. A scleral channel which extends from the scleral surface to the anterior segment is then created using a needle body. The silicone tube is inserted through the scleral channel to enter the ocular anterior chamber. The silicone tube is then either completely or partially occluded using sutures to limit fluid flow and regulate pressure.

Newer aqueous drainage devices such as the MicroShunt device (U.S. Pat. No. 9,101,444) consists of a straight tube of about 8 mm in length with integrated tabs spaced intermediate proximal and distal ends of the tube. The entire length of the device is straight and comprises a microcapillary lumen with an internal diameter of about 0.07 mm which is dimensioned to provide resistance to fluid flow preventing IOP from falling below 5 mmHg. A scleral channel is created using a needle body to enter the anterior chamber. The distal end of the tube is passed through the scleral channel to enter the anterior chamber. The tabs are positioned in the scleral channel to create a fluid seal between the tube and surrounding scleral tissue. The proximal end is then left lying in the subconjunctival space to create a bleb roughly 6 mm from the limbus.

Existing glaucoma drainage devices suffer from a number of shortcomings which may increase the risk of aqueous fluid leakage, hypotony, filtration failure, endothelial cell damage and device migration. These shortcomings include:

1. Drainage devices such as the Baerveldt device and the Microshunt device create a bleb at a pre-determined distance from the limbus. This prevents the surgeon from being able to create a bleb at a position of their choosing where they feel it will have the lowest risk of scarring and filtration failure.
2. Drainage devices such as the Microshunt device include a capillary valve which traverses the entire length of the drainage device. This means the devices cannot be cut to the required length without significantly altering the resistance to fluid flow.
3. Drainage devices such as the Baerveldt and MicroShunt devices comprise straight tubing for traversing a scleral channel to enter the anterior chamber. This means that the direction of the tubing is aimed towards the corneal endothelium which is a risk for endothelial cell damage. It is desirable for tubing to travel in a direction parallel to the iris plane when entering the anterior or posterior chamber of the eye.
4. Drainage devices such as the Baerveldt device do not include a built-in flow resistance mechanism such as a leaf or capillary valve. This requires the surgeon to tie off the tubing using sutures for a period of time until the bleb has formed. This makes surgery more complex and delays the pressure lowering effect of such devices.
5. Drainage devices such as the MicroShunt device include locating tabs having rounded symmetrical outer profiles which provide minimal resistance to migration when implanted in a scleral channel. This means that relatively small longitudinal forces applied to the tubing can result in unwanted migration of the device along the scleral channel.
6. Drainage devices such as the Baerveldt and MicroShunt are provided either with, or without, a footplate respectively which means the surgeon cannot choose whether or not they feel a footplate is indicated for the specific patient.
7. Drainage devices such as the Baerveldt and MicroShunt provide a fixed resistance to fluid flow which cannot be tailored to the individual patient's aqueous production rate or allowed to vary depending on time after surgery.

It is an object of the present invention to provide a shunt and a method for treating glaucoma which addresses the abovementioned shortcomings.

In this specification, the term "distal" means in the direction of the eye of a patient or away from a user of the shunt, while the term "proximal" means in the direction away from the eye of the patient or towards the user of the shunt.

SUMMARY OF INVENTION

The first aspect of the invention is provided a shunt for treating glaucoma by lowering intraocular pressure in an eye of a patient, the shunt having an elongate duct defining a fluid passageway for diverting aqueous humor from a chamber of the eye, the elongate duct having a distal end and an opposite proximal end, the distal end being implantable in the chamber of the eye, and a fixation body extending outwardly from the elongate duct, the shunt being characterized in that the elongate duct has a distal portion defining the distal end of the duct, which is locatable in the scleral channel of the patient, the distal portion being deformable so as to permit the distal portion to conform to anatomical structures of the eye of the patient and being of a severable material in order to permit a surgeon to cut the distal portion to a desired length corresponding to a desired location for the formation of a bleb into which aqueous humor can drain, and a proximal portion, defining the proximal end of the elongate duct.

The distal portion has a distal lumen defining a distal part of the fluid passageway and the proximal portion has a proximal capillary lumen which is in fluid flow communication with the distal lumen, the proximal lumen having an internal diameter which is relatively smaller than an internal diameter of the distal lumen so as to reduce a flow rate of aqueous humor and regulate pressure along the proximal capillary lumen sufficient to prevent hypotony.

The fixation body of the shunt is slidably located on the distal portion of the elongate duct for fixing the distal portion of the duct within the scleral channel at a desired position determined by a required length of the shunt.

The chamber of the eye in which the shunt is implanted may be the anterior chamber or the posterior chamber or the vitreous chamber of the eye.

The shunt may be configured to resist aqueous fluid flow at flow rates of between 1.5 to 3.0 micromillimetres per minute through the shunt using the Haigen Pouseille equation and a viscosity factor of 7.042 cP. More specifically, the shunt may be configured to resist aqueous fluid flow at flow rates of about 2 micromillimetres per minute through the shunt.

The distal lumen may have a diameter of between 0.12 mm and 0.3 mm. More specifically, the distal lumen may have a diameter of about 0.2 mm.

The proximal capillary lumen may have a diameter of between 0.035 mm and 0.06 mm. More specifically, the diameter of the proximal capillary lumen may be about 0.05 mm.

The distal portion may have a length of between 4 mm and 30 mm after cutting by the surgeon. The proximal portion may have a length of between 1 mm and 8 mm. More specifically, the proximal portion may have a length of around 5 mm.

The distal portion may be configured to provide negligible fluid flow resistance less than 1 mmHg while the proximal capillary portion may be configured to provide significant fluid flow resistance of between 4 mmHg and 12 mmHg.

The internal diameter of the distal lumen may be relatively larger than an internal diameter of the proximal lumen in a ratio of between 2 and 8 times larger.

The length of the distal portion may be relatively longer than the length of the proximal portion in a ratio of between 2 and 30 times longer.

In a second embodiment of the elongate duct, the proximal portion may comprise an inner wall and an outer wall, wherein the inner wall comprises a dissolvable substance which dissolves over a period of between 4 and 12 weeks, in order to facilitate adjustment of internal resistance to fluid flow through the proximal portion of the elongate duct.

The proximal portion of the elongate duct may be releasably connected to the distal portion of the elongate duct. Alternatively, the proximal portion of the elongate duct may be fixedly connected to the distal portion of elongate duct.

The shunt may include a scleral footplate which is operatively connected to the proximal end of the elongate duct for fixing the proximal end of the elongate duct to the sclera at the location of formation of the bleb and for enlarging the surface area over which aqueous fluid drains.

The proximal end of the elongate duct may be releasably connected to the footplate. Alternatively, the proximal end of the elongate duct may be fixedly connected to the footplate.

The proximal portion of the elongate duct may have a rigid construction. The proximal portion may have an oval shape when viewed in cross section. The proximal portion may have a curvature that conforms to an anatomical curvature of the ocular globe.

The fixation body may be frictionally located on the distal portion of the elongate duct in an arrangement wherein a coefficient of friction acting between the fixation body and the elongate duct is sufficient to adequately resist movement of the fixation body relative to the elongate duct when the elongate duct is implanted in the scleral channel of the patient yet permits sliding displacement of the fixation body relative to the elongate duct when a moderate force is applied to the fixation body by a surgeon.

The fixation body may define an internal passage within which the elongate duct is received. The fixation body may be located on the elongate duct in an interference fit wherein an internal diameter of the fixation body is slightly less than an external diameter of the distal portion of the elongate duct.

The internal passage of the fixation body and the distal portion of the elongate duct may be cylindrical.

The fixation body may have a pair of laterally-extending flanges which project outwardly from opposite sides thereof.

The fixation body may have a convexly rounded lower surface and a substantially flat upper surface.

The fixation body may be of a rigid construction.

The fixation body may have an upper body portion which engages an upper side of the distal portion and a lower body portion which engages a lower side of the distal portion of the elongate duct, the upper body portion being relatively wider than the lower body when viewed in side view. The asymmetrical shape of the fixation body resists displacement of the shunt within a scleral channel created within scleral tissue. The asymmetrical shape furthermore causes bending in the distal portion at regions thereof adjacent opposite proximal and distal sides of the fixation body so as to direct the distal end away from the corneal endothelium and towards the iris plane.

In a particular embodiment of the fixation body, the fixation body may define a curved internal passage in which the elongate duct is received. The curvature of the internal passage causes bending of the elongate duct received therein, thereby resisting displacement of the shunt within a scleral channel created within scleral tissue thereby to resist displacement of the shunt within a scleral channel created within scleral tissue and direct the distal end away from the corneal endothelium and towards the iris plane of the patient.

In a third embodiment of the elongate duct, the distal portion may comprise a wall thickness or diameter which varies along the length of the tube in order to facilitate adjustment of the internal resistance to fluid flow through the distal portion. More specifically, in a first example of the third embodiment, the outer diameter of the distal portion may taper along at least along a portion of the length of the distal portion, with the wall thickness remaining constant, providing the lumen of the distal portion with a tapered configuration. In a second example of the third embodiment, the wall thickness of the distal portion may taper along at least a portion of the length of the distal portion, with the outer diameter remaining constant, providing the lumen of the distal portion with a tapered configuration. In use, the internal resistance to fluid flow through the distal portion can be adjusted by moving the position of the fixation body along the distal portion in the region of the tapered lumen in order to provide for variations in patient aqueous fluid production rates.

According to a second aspect of the invention there is provided a surgical method for treating glaucoma in a patient by lowering intraocular pressure in an eye of a patient, the surgical method may include: opening the conjunctival/tenon's complex to create a pocket between the conjunctival/tenon's complex and the sclera. The method may also include providing the shunt as defined and described hereinabove in accordance with the first aspect of the invention. The method may further include sliding the fixation body along the distal portion of the elongate duct until a desired fixation body position is achieved corresponding to a desired length of the distal portion of the elongate duct and a desired position of the fixation body along the elongate duct for fixing the distal portion at a desired position relative to the limbus. The method may also include cutting the distal portion of the elongate duct so as to adjust a length of the elongate duct and using a surgical instrument, creating a passageway through scleral tissue so as to form a scleral channel from an external position at the pocket in the conjunctival/tenon's complex to the chamber of the eye from which aqueous fluid is to be diverted. The method may also include inserting the distal portion of the elongate duct of the shunt into the scleral channel until the distal end of the elongate duct lies within the chamber of the eye, and closing the conjunctival/tenon's complex leaving the proximal end of the shunt lying within the pocket.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

DETAILED DESCRIPTION FOR CARRYING OUT THE INVENTION

Figure 1:
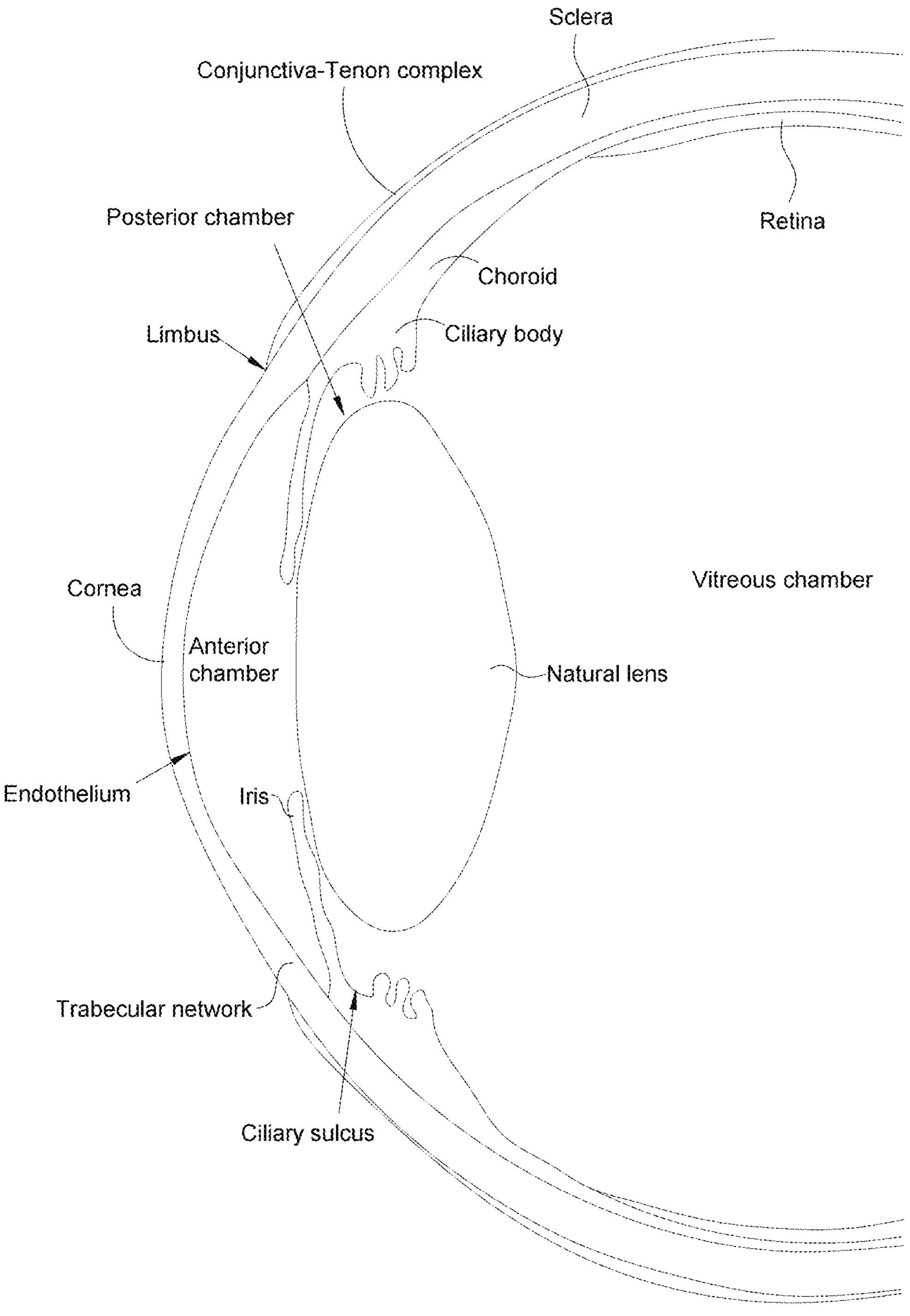
FIG. 1 shows an illustration providing the anatomic details of a human eye, in accordance with an aspect of the present disclosure.
Figure 2:
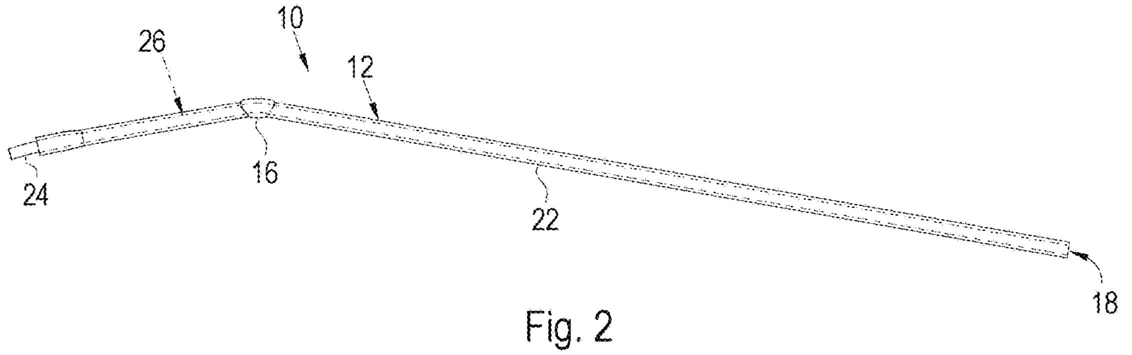
FIG. 2 shows a side view of a shunt for treating glaucoma, prior to cutting the shunt to a desired length, in accordance with an aspect of the present disclosure.
Figure 3:
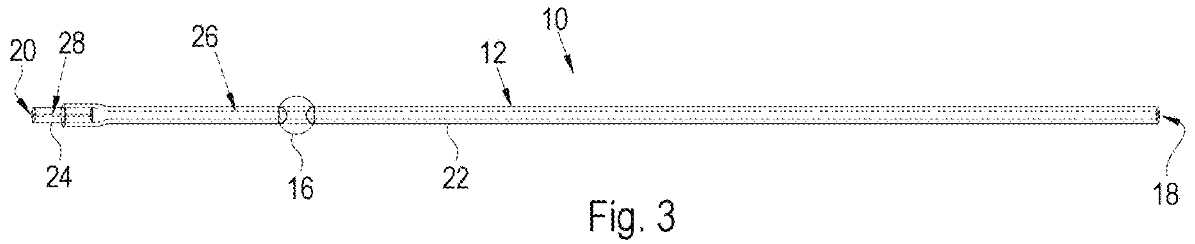
FIG. 3 shows top plan view of the shunt of FIG. 2, in accordance with an aspect of the present disclosure.
Figure 4:
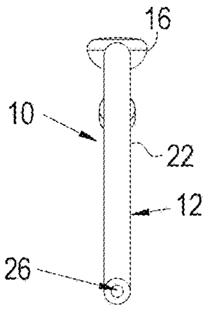
FIG. 4 shows a distal end view of the shunt of FIG. 2, in accordance with an aspect of the present disclosure.
Figure 5:
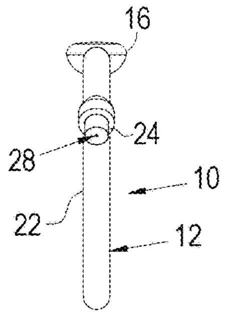
FIG. 5 shows a proximal end view of the shunt of FIG. 2, in accordance with an aspect of the present disclosure.

With reference to the drawings, a shunt for treating glaucoma by lowering intraocular pressure in an eye of a patient, is designated by the reference numeral 10.

With reference to FIGS. 2-10, the shunt 10 comprises, broadly, an elongate silicone rubber duct 12 for defining a fluid passageway 14 for diverting aqueous humor from a chamber of the patient's eye and a fixation body 16 extending outwardly from the duct 12 for fixing the duct within tissue surrounding the eye. The relevant chamber of the eye may be the anterior chamber or the posterior chamber of the eye.

The elongate duct 12 has a distal end 18 and an opposite proximal end 20, the distal end 18 being implantable in the relevant chamber of the eye. The elongate duct has a distal portion 22 defining the distal end of the duct, which is locatable in the scleral channel of the patient, the distal portion being deformable so as to permit the distal portion to conform to anatomical structures of the eye of the patient.

Figure 6:
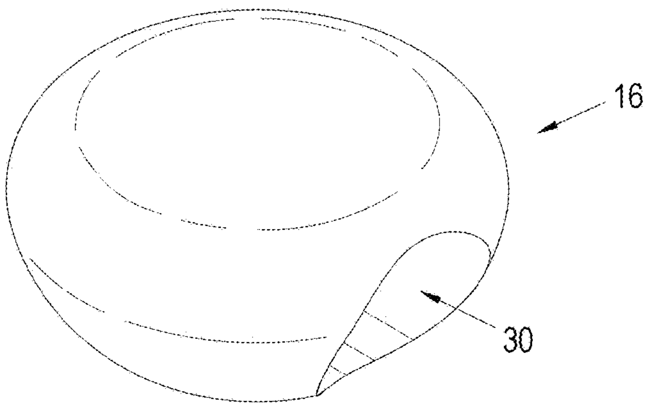
FIG. 6 shows a perspective view as seen from above of the fixation body of the shunt of FIG. 2, in accordance with an aspect of the present disclosure.
Figure 7:
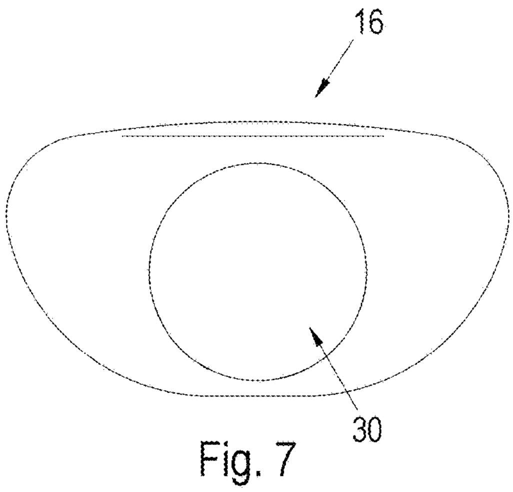
FIG. 7 shows an end view of the fixation body, in accordance with an aspect of the present disclosure.
Figure 8:
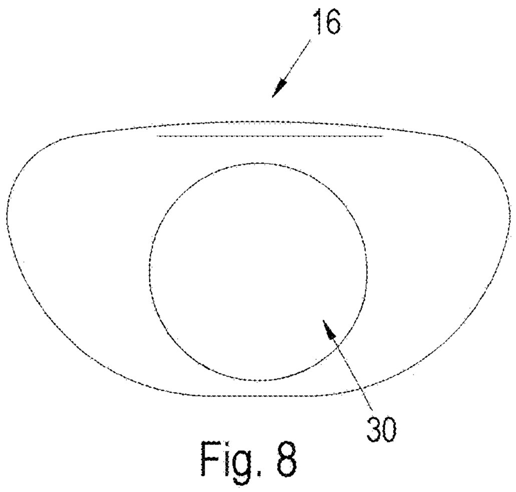
FIG. 8 shows an opposite end view of the fixation body, in accordance with an aspect of the present disclosure.
Figure 9:
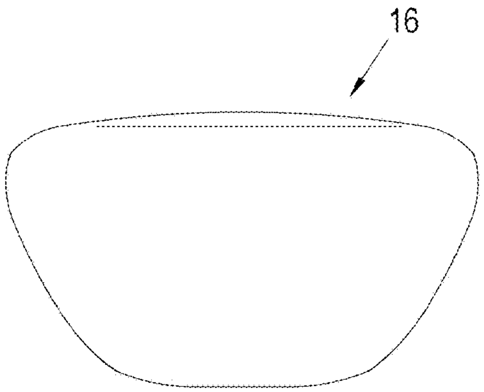
FIG. 9 shows a side view of the fixation body, in accordance with an aspect of the present disclosure.
Figure 10:
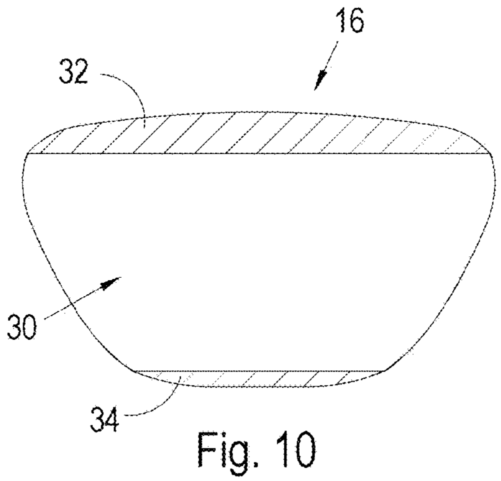
FIG. 10 shows a sectional side view of the fixation body, in accordance with an aspect of the present disclosure.

The distal portion is also severable, allowing a surgeon to cut the distal portion to a desired length corresponding to the anatomical dimensions of the patient's eye and required bleb position. As is illustrated in FIGS. 6-8, a bevel cut is made in the distal portion so as to define a relatively sharp point at a distal end 18.1 for facilitating insertion of the distal portion along a channel defined in scleral tissue.

The elongate duct 12 further has a proximal portion 24 having a rigid construction, which defines the proximal end of the elongate duct.

The distal portion 22 has a distal lumen 26 defining a distal part of the fluid passageway and the proximal portion 24 has a proximal capillary lumen 28 which is in fluid flow communication with the distal lumen, the proximal lumen having an internal diameter which is relatively smaller than an internal diameter of the distal lumen so as to reduce a flow rate of aqueous humor along the proximal capillary lumen.

The shunt is configured to resist aqueous fluid flow at flow rates of between 1.5 to 3.0 micromillimetres per minute through the shunt using the Haigen Pouseille equation and a viscosity factor of 7.042 cP and more specifically, about 2 micromillimetres per minute.

The distal lumen has a diameter of between 0.12 mm and 0.3 mm. More specifically, the distal lumen has a diameter of about 0.2 mm.

The proximal capillary lumen has a diameter of between 0.035 mm and 0.06 mm. More specifically, the diameter of the proximal capillary lumen is about 0.05 mm.

The distal portion has a length of between 4 mm and 30 mm after cutting by the surgeon.

The proximal portion has a length of between 1 mm and 8 mm. More specifically, the proximal portion has a length of around 5 mm. The distal portion is configured to provide negligible fluid flow resistance less than 1 mmHg while the proximal capillary portion is configured to provide significant fluid flow resistance of between 4 mmHg and 12 mmHg.

The internal diameter of the distal lumen is relatively larger than an internal diameter of the proximal lumen in a ratio of between 2 and 8 times larger.

The length of the distal portion is relatively longer than the length of the proximal portion in a ratio of between 2 and 30 times longer.

In a particular embodiment of the invention, the proximal portion of the elongate duct is releasably connected to the distal portion of the elongate duct. In another embodiment of the invention, the proximal portion of the elongate duct is fixedly connected to the distal portion of elongate duct.

The proximal portion of the elongate duct has an oval shape when viewed in cross section. The proximal portion has a curvature that conforms to that of an anatomical curvature of the ocular globe.

The fixation body 14 of the shunt forms an effective seal with surrounding scleral tissue. The fixation body is slidably located on the distal portion of the elongate duct 12 for fixing the distal portion 22 of the duct within a channel created in scleral tissue at a desired position determined by a required length of the shunt as will be explained in more detail hereinbelow.

The fixation body 14 is frictionally located on the distal portion 22 of the elongate duct in an arrangement wherein a coefficient of friction acting between the fixation body and the elongate duct is sufficient to adequately resist movement of the fixation body relative to the elongate duct following implantation yet permit sliding displacement of the fixation body relative to the elongate duct when a force is applied to the fixation body by a surgeon during implantation.

The fixation body defines an internal passage 30 within which the distal portion of the elongate duct is received. The internal passage 30 of the fixation body and the distal portion of the elongate duct are cylindrical. The fixation body has an upper body portion 32 which engages an upper side of the distal portion and a lower body portion 34 which engages a lower side of the distal portion, the upper body portion being relatively wider than the lower body when viewed in side view. The asymmetrical shape of the fixation body resists displacement of the shunt within a scleral channel created within scleral tissue and causes bending in the distal portion away from the endothelium.

With reference to FIGS. 11-20, the manner in which the shunt 10 is implanted in the anterior chamber of an eye of a patient, is illustrated. The anatomical dimensions and ideal bleb location of the eye of the patient are initially measured by the surgeon performing a visual observation of the patient's eye in order to determine an optimal length for the shunt.

Figure 11:
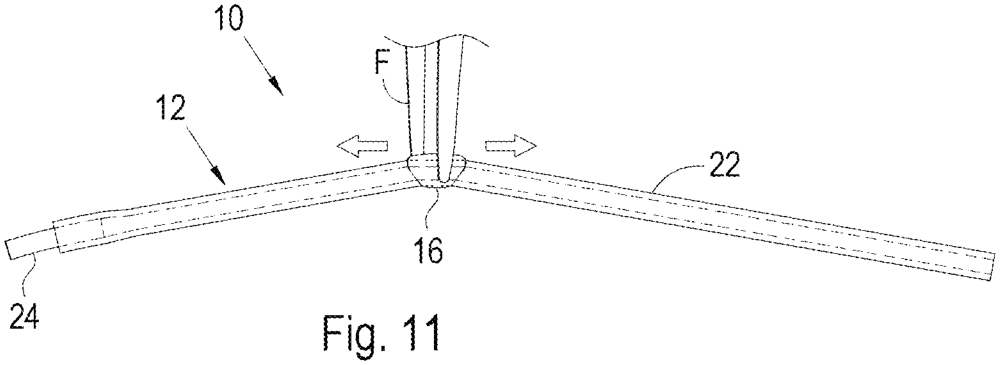
FIG. 11 shows a side view of the shunt of FIG. 2, illustrating the manner in which the fixation body is displaced along the distal portion of the elongate duct using forceps, in accordance with an aspect of the present disclosure.

With specific reference to FIG. 11, the fixation body 16 is then slid along the distal portion of the elongate duct by a surgeon gripping the fixation body 16 using forceps and applying a force to the fixation body in a direction for displacing the fixation body along the distal portion until a desired position along the distal portion is achieved. An important consideration in this regard is the position at which the surgeon would like to form a bleb into which aqueous humor from the anterior chamber is allowed to drain after implantation of the shunt.

Figure 15:
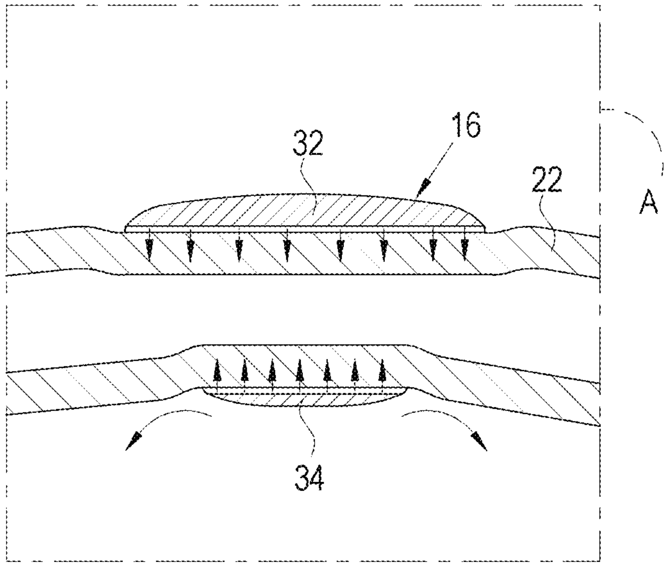
FIG. 15 shows enlarged detail A of FIG. 14, in accordance with an aspect of the present disclosure.

As is more clearly illustrated in FIG. 15, an internal diameter of the internal passage 30 of the fixation body is slightly less than an external diameter of the distal portion of the elongate duct, causing the fixation body to be located on the distal portion 22 of the duct 12 in an interference fit permitting sliding displacement of the fixation body when sufficient force is applied to the fixation body in order to overcome frictional forces holding the fixation body on the distal position.

Figure 12:
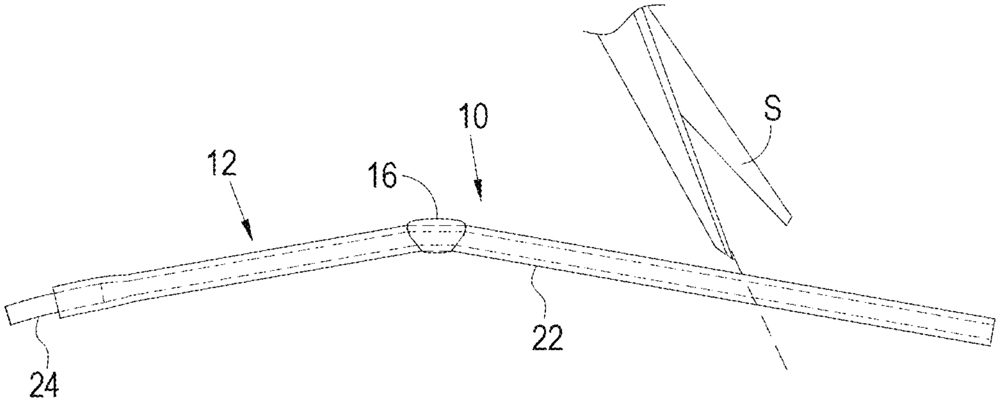
FIG. 12 shows a side view of the shunt of FIG. 2, illustrating the manner in which the distal portion of the elongate duct is cut by a surgeon, in accordance with an aspect of the present disclosure.
Figure 13:
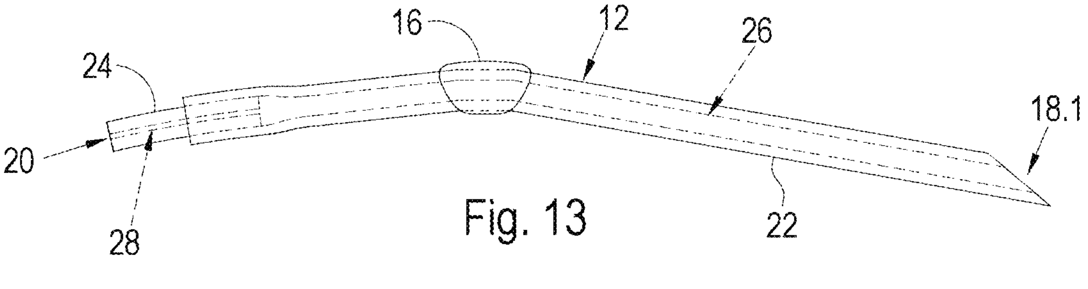
FIG. 13 shows a side view of the shunt of FIG. 2 after it has been cut to a desired length, in accordance with an aspect of the present disclosure.
Figure 14:
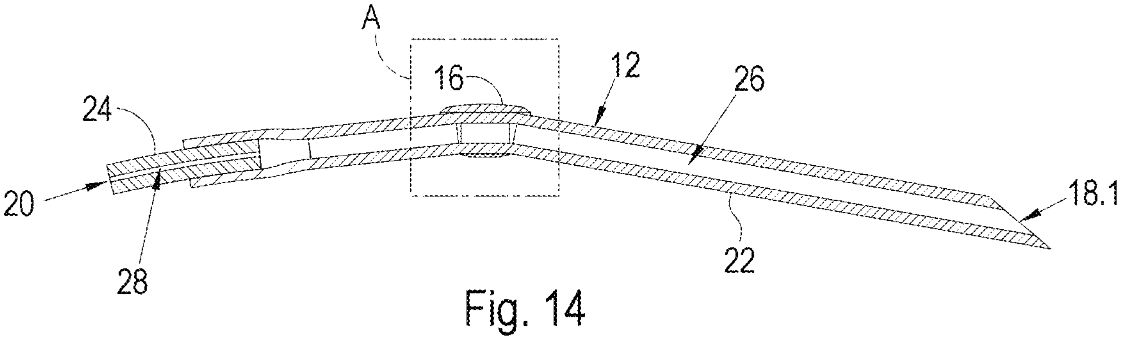
FIG. 14 shows a sectional side view of the shunt of FIG. 13, in accordance with an aspect of the present disclosure.

With reference to FIGS. 12-14, a distal portion 22 of the elongate duct 12 of the shunt is then cut by a surgeon using surgical scissors S, so as to adjust the length of the shunt to a desired length. More specifically, an angled bevel cut is made in the distal portion so as to provide a distal end 18.1 having a sharp point for facilitating insertion of the distal portion along the scleral channel and into the anterior or posterior chamber.

Figure 16:
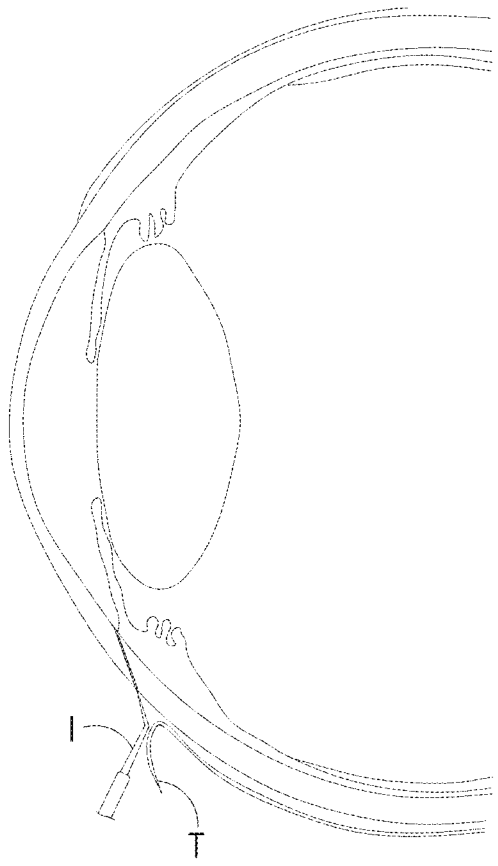
FIG. 16 shows the manner in which a channel is created in the sclera using a surgical instrument for insertion of the shunt of FIG. 2 into the anterior chamber of the eye of the patient, in accordance with an aspect of the present disclosure.

With reference to FIG. 16, a portion T of the conjunctiva-tenon's complex is released from the limbus and retracted. A passageway is then created through scleral tissue by a surgeon using a surgical blade I so as to form a scleral channel from an external position having an entry point approximately 3 mm from the limbus to an exit point into the anterior chamber at the trabecular network. The distal portion of the elongate duct of the shunt is then inserted into the scleral channel until the fixation body lies within the scleral channel and the distal end of the elongate duct lies within the anterior chamber.

Figure 17:
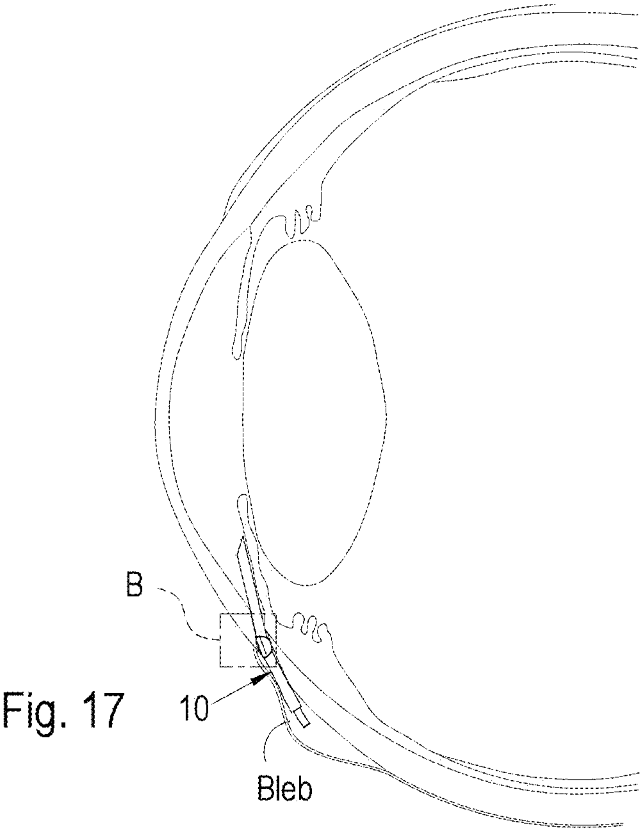
FIG. 17 shows the shunt of FIG. 2 wherein the distal portion is cut so as to provide a relatively short section of tubing and implanted in the anterior chamber of the patient's eye and creating a bleb near to the limbus, in accordance with an aspect of the present disclosure.
Figure 18:
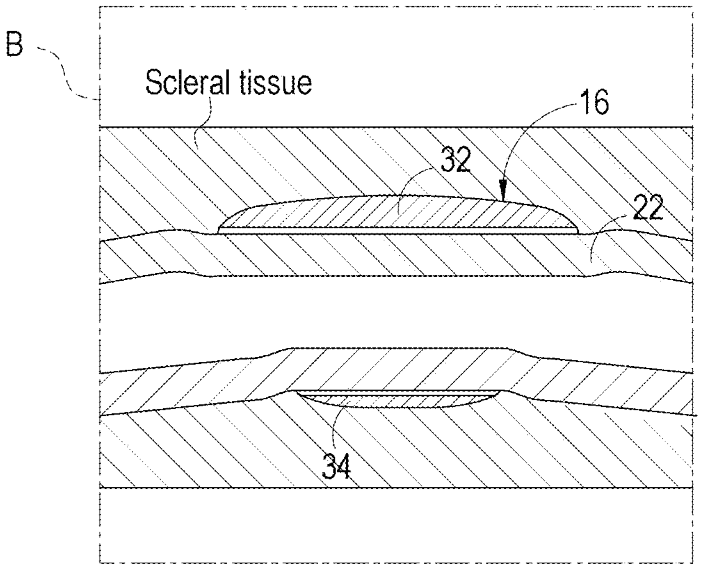
FIG. 18 shows enlarged detail B of the shunt of FIG. 17, in accordance with an aspect of the present disclosure.

In FIG. 17, the shunt 10 is shown implanted in the anterior chamber of the patient's eye, providing a passageway along which aqueous humor is drained from the anterior chamber into a bleb formed between scleral tissue and the conjunctiva-tenon's complex near to the limbus. In FIG. 18, the manner in which the fixation body grips scleral tissue within the scleral channel, is illustrated.

Figure 19:
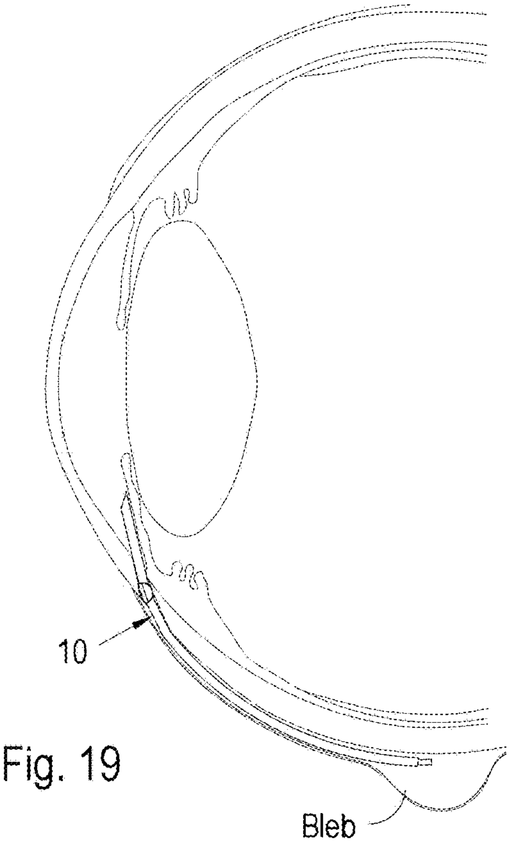
FIG. 19 shows the implanted shunt of FIG. 2 wherein the distal portion is cut so as to provide a relatively long section of tubing and implanted in the anterior chamber of the patient's eye and creating a bleb away from the limbus, in accordance with an aspect of the present disclosure.
Figure 20:
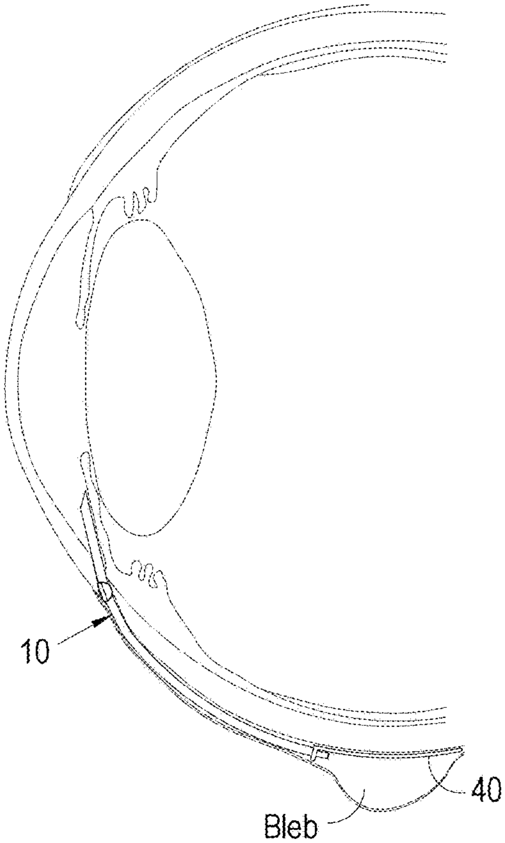
FIG. 20 shows the implanted shunt of FIG. 17 with a shorter extension tube and a footplate connected thereto so as to adjust the size and position at which a bleb is formed, in accordance with an aspect of the present disclosure.

With reference to FIG. 19, a shunt 10 wherein the fixation body has been adjusted to be closer to the distal end and the shunt has been cut short to effectively adjust the position at which a bleb is formed, is shown With reference to FIG. 20, the shunt 10 is shown with a Baerveldt device 40 attached thereto and located at a base of a bleb formed between scleral tissue and the conjunctiva-tenon's complex.

Figure 21:
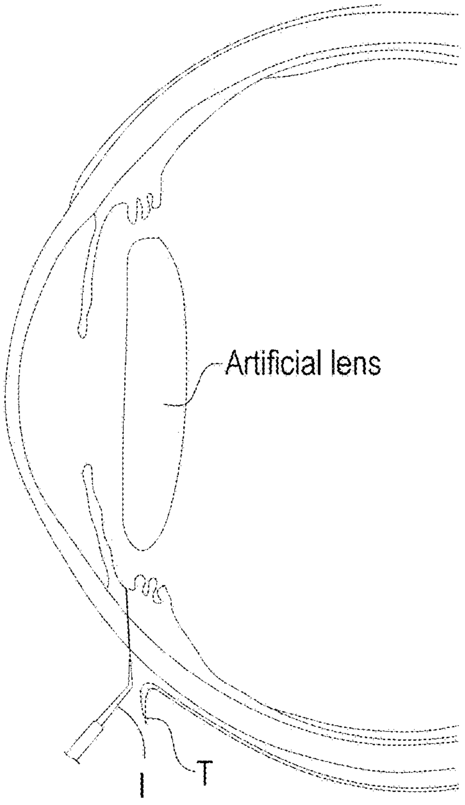
FIG. 21 illustrates the manner in which a channel is created in the sclera using a surgical instrument for insertion of the shunt of FIG. 2 into the posterior chamber of the eye of the patient, in accordance with an aspect of the present disclosure.
Figure 22:
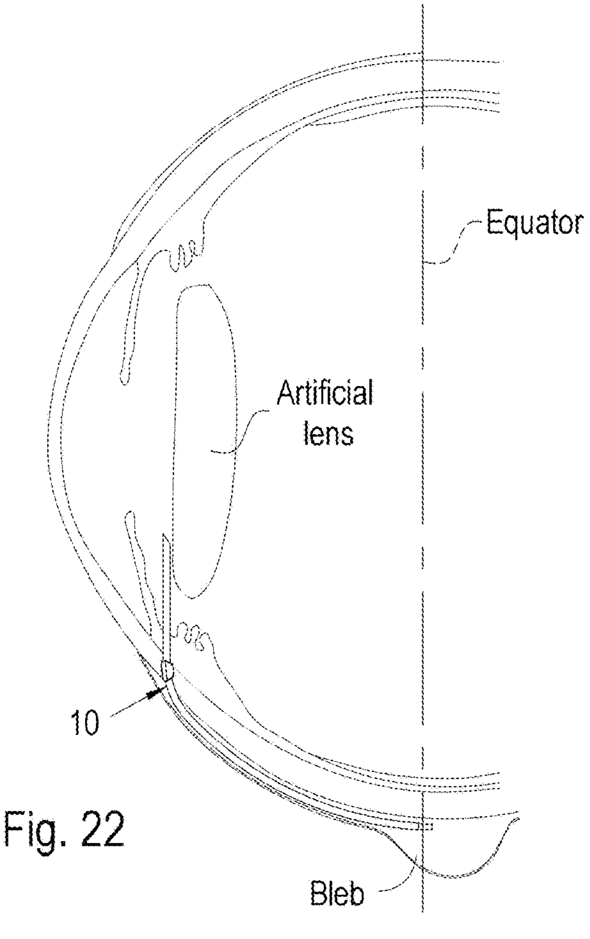
FIG. 22 shows the shunt of FIG. 2, implanted in the posterior chamber of the eye, in accordance with an aspect of the present disclosure.

With reference to FIGS. 21 and 22, the manner in which the shunt 10 is implanted in the posterior chamber of an eye and used, is illustrated. The shunt 10 is implanted in the same manner as described above in relation to the implantation of the shunt into the anterior chamber of the eye, with the only difference being that the scleral channel is formed with an exit point into the posterior chamber at the ciliary sulcus.

The shunt 10 provides an extended length of deformable tube with a fixation body slidably located thereon so as to allow a surgeon to adjust the position of the fixation body along the elongate duct to thereby adjust the length of the shunt to the anatomical dimensions of the eye of a patient and provide for optimal positioning of a bleb into which aqueous humor can drain.

The proximal portion of the elongate duct provides the shunt with a capillary valve, while the distal portion of the elongate duct may be cut so as to adjust the length of the shunt without affecting the capillary valve or altering the resistance to fluid flow along the fluid passageway of the shunt significantly.

The interference fit of the fixation body on the distal portion of the shunt provides for resistance to migration of the fixation body along the elongate duct when the shunt is implanted, while allowing for movement along the distal portion in order to adjust the length of the shunt. The outwardly projecting formations furthermore create a fluid seal in the scleral channel.

The asymmetrical shape of the fixation body resists displacement of the shunt within a scleral channel created within scleral tissue and creates a bend away from the endothelium as described hereinabove.

Figure 23:
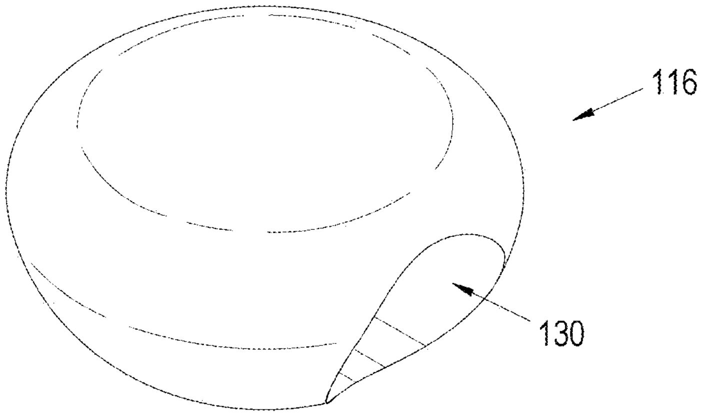
FIG. 23 shows a perspective view as seen from above of another embodiment of a fixation body of the shunt in accordance with the invention, in accordance with an aspect of the present disclosure.
Figure 24:
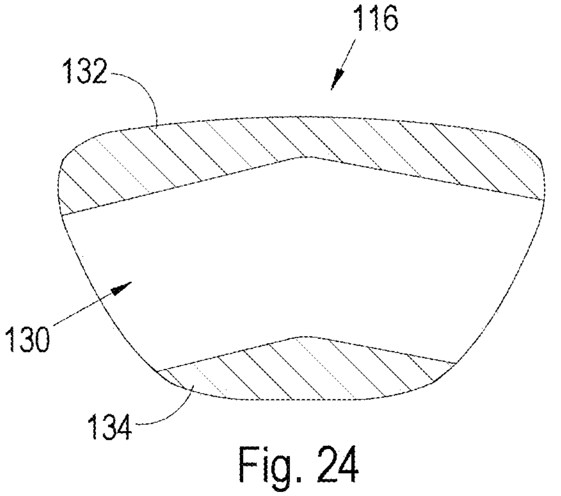
FIG. 24 shows a sectional side view of the fixation body of FIG. 23, in accordance with an aspect of the present disclosure.

FIGS. 23 and 24 show another embodiment of a fixation body of the shunt in accordance with the invention, which is designated by the reference numeral 116. The fixation body 116 is similar to the fixation body and those features of the fixation body 116 which are the same as and/or the similar to those of the fixation body 16 are designated in FIGS. 23 and 24 by the same and/or similar reference numerals. The fixation body 116 defines a curved internal passage 130 in which the distal portion 22 of the elongate duct is received, the curvature of the internal passage 130 being configured so as to cause bending of the elongate duct when the elongate duct is received therein, thereby to resist displacement of the shunt within a scleral channel created within scleral tissue and direct the distal end away from the corneal endothelium and towards the iris plane of the patient.

Figure 25:
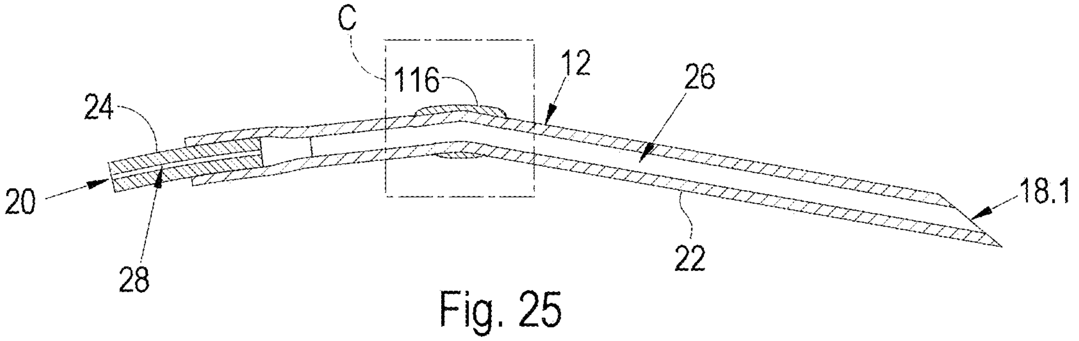
FIG. 25 shows a sectional side view of the shunt including the fixation body of FIG. 23, in accordance with an aspect of the present disclosure.
Figure 26:
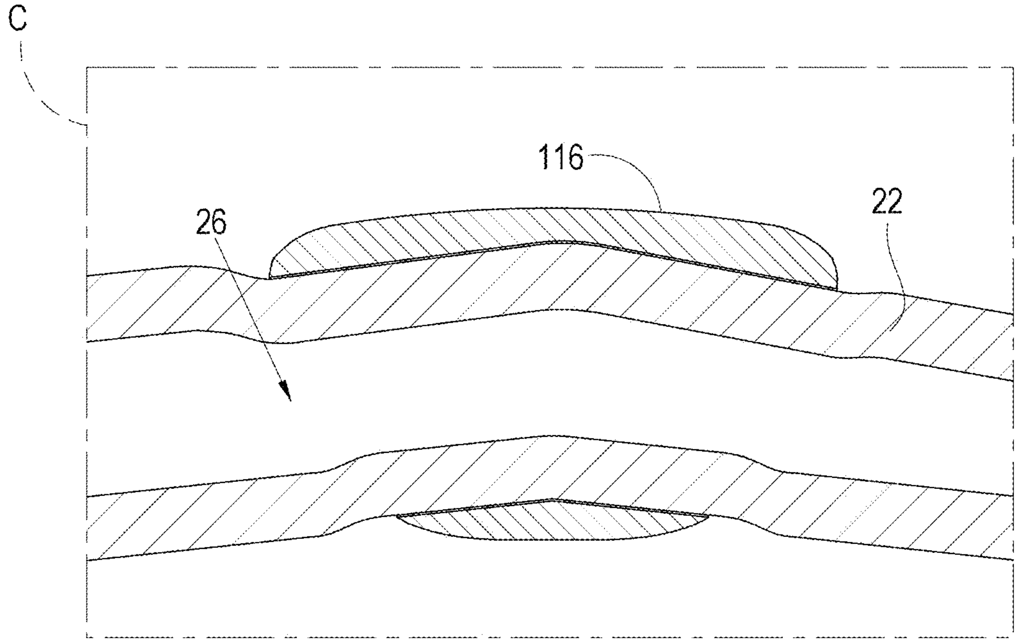
FIG. 26 shows enlarged detail C of the shunt of FIG. 25, in accordance with an aspect of the present disclosure.

FIGS. 25 and 26 show a shunt in accordance with the invention, including the fixation body 116, illustrating the manner in which the elongate duct is bent by the fixation body.

Figure 27:
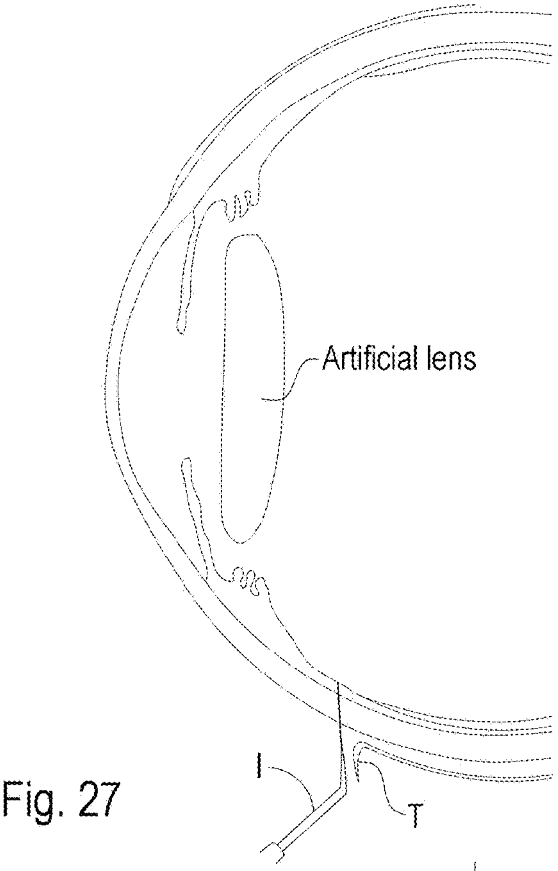
FIG. 27 shows the manner in which a channel is created in the sclera using a surgical instrument for insertion of the shunt of FIG. 2 into the vitreous chamber of the eye of the patient, in accordance with an aspect of the present disclosure.
Figure 28:
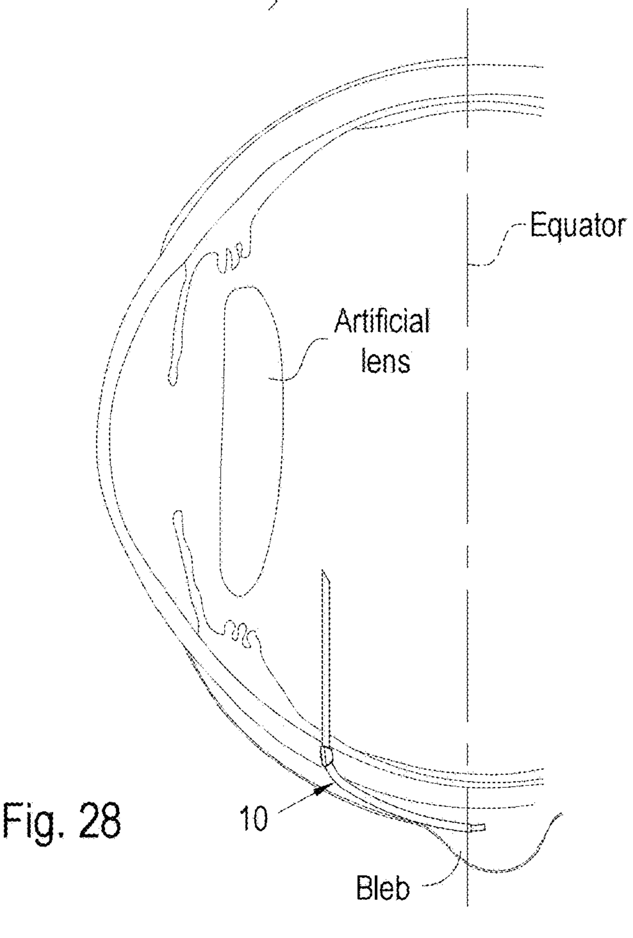
FIG. 28 shows the shunt of FIG. 2, implanted in the vitreous chamber of the eye, in accordance with an aspect of the present disclosure.

With reference to FIGS. 27 and 28, the manner in which the shunt 10 is implanted in the vitreous chamber of an eye and used, is illustrated. The shunt 10 is implanted in the same manner as described above in relation to the implantation of the shunt into the anterior chamber of the eye, with the only difference being that the scleral channel is formed in the pars plana region of the ciliary body with an exit point into the vitreous chamber.

Figure 29:
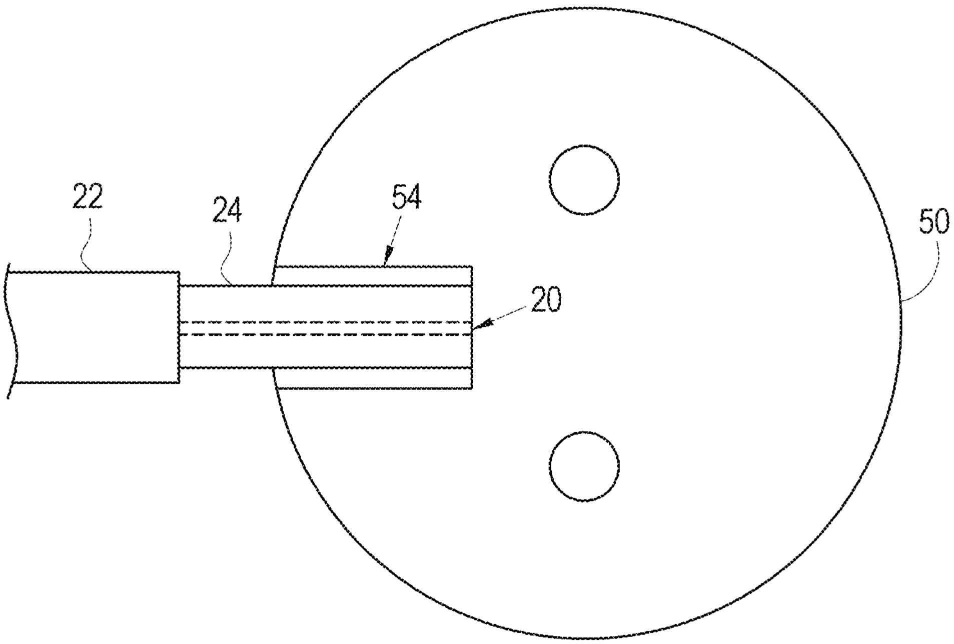
FIG. 29 shows an enlarged fragmentary plan view of the proximal end of the elongate duct attached to a scleral footplate, in accordance with an aspect of the present disclosure.
Figure 30:
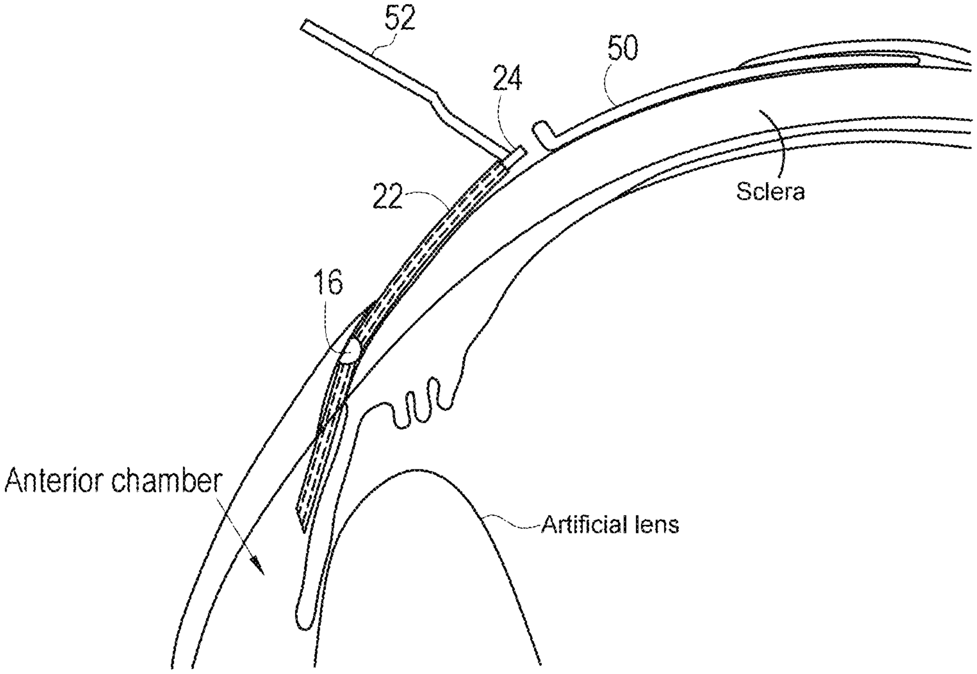
FIG. 30 shows the manner in which the shunt of FIG. 2 is attached to the scleral footplate of FIG. 29, in accordance with an aspect of the present disclosure.
Figure 31:
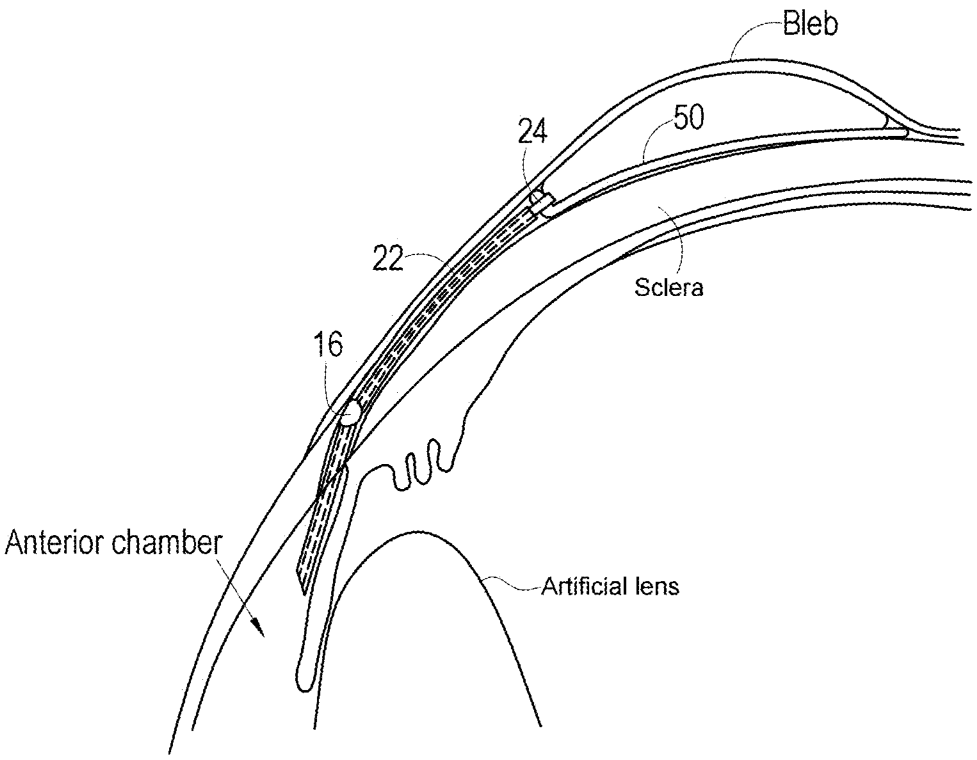
FIG. 31 shows the proximal end of the elongate duct of the shunt of FIG. 2 attached to the scleral footplate of FIG. 29, with the distal end implanted in the anterior chamber of the eye, in accordance with an aspect of the present disclosure.

With reference to FIGS. 29-31, the shunt 10 includes a scleral footplate 50 which is operatively connected to the proximal end 20 of the elongate duct 12 for fixing the proximal end of the elongate duct to the sclera at the location of formation of a bleb. The proximal shunt portion 24 is gripped by a surgeon using forceps 52 and attached to a receiving recess 54 in the footplate. The proximal end of the elongate duct may be releasably connected to the footplate. Alternatively, the proximal end of the elongate duct may be fixedly connected to the footplate. The scleral footplate increases the surface area of the bleb in patients with generally unhealthy conjunctiva.

Figure 32:
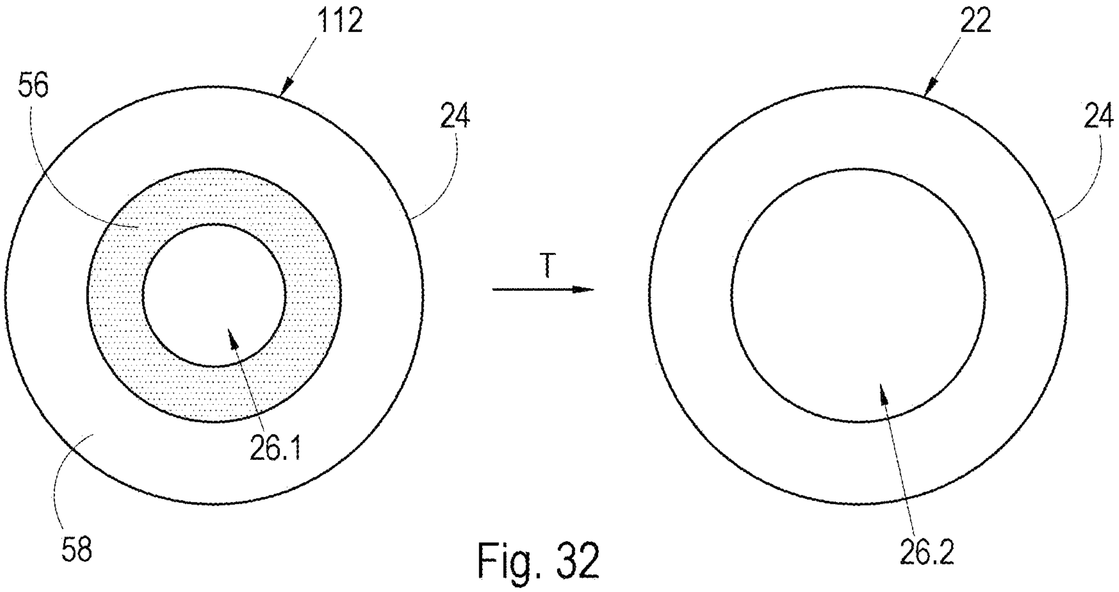
FIG. 32 shows second embodiment of the elongate duct wherein the proximal portion has an inner wall and an outer wall and wherein the inner wall comprises a dissolvable substance, in accordance with an aspect of the present disclosure.

With reference to FIG. 32, a second embodiment of the elongate duct is designated by the reference numeral 112. The duct 112 is similar to the elongate duct 12, with the only difference being that the proximal portion 24 initially comprises an inner wall 56 in addition to an outer wall 58, wherein the inner wall 56 comprises a dissolvable substance which dissolves over a period T of between 4 and 12 weeks, in order to facilitate adjustment of internal resistance to fluid flow through the proximal portion of the elongate duct. At the beginning of the period T, the inner wall provides a relatively high degree of resistance which gradually decreases as the inner wall dissolves until the inner wall is dissolved at the end of the period T as shown in FIG. 32. The inner wall 56 defines a relatively narrow lumen 26.1 initially and after the inner wall has dissolved the outer wall defines a larger diameter lumen 26.2.

Figure 33:
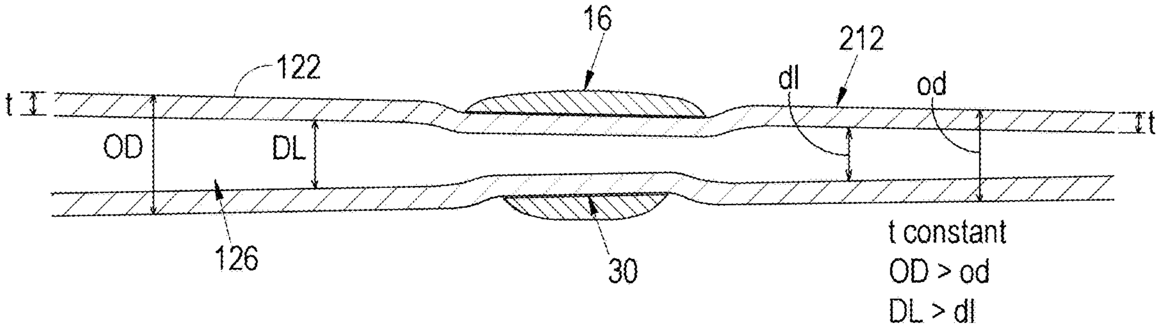
FIG. 33 shows a third embodiment of the elongate duct wherein the distal portion has a diameter which varies along the length of the distal portion, in accordance with an aspect of the present disclosure.

With reference to FIG. 33, a first example of a third embodiment of the elongate duct is designated by the reference numeral 212. The elongate duct has a distal portion 122 having a constant wall thickness and an outer diameter which varies (from a relatively larger outer diameter OD to a relatively smaller outer diameter od) along the length of the distal portion. The outer diameter of the distal portion 122 is greater than the internal diameter of the internal passage 30 of the fixation body 16 such that when the distal portion 122 is received in the internal passage 30, the wall of the distal portion deforms inwardly. The diameter of the distal portion tapers along at least along a portion of the length of the distal portion, such that the lumen 126 has a tapered configuration. The diameter of the lumen 126 tapers from a relatively larger diameter DL to a relatively smaller diameter dl, with the wall thickness t remaining constant. In use, the internal resistance to fluid flow through the distal portion can be adjusted by moving the position of the fixation body along the distal portion in order to provide for variations in patient aqueous fluid production rates. The elongate duct 212 is pinched by the fixation body 16 when it is received in the internal passage 30 of the fixation body, causing inward deformation of the duct in the region of the fixation body and thereby narrowing of the lumen.

Figure 34:
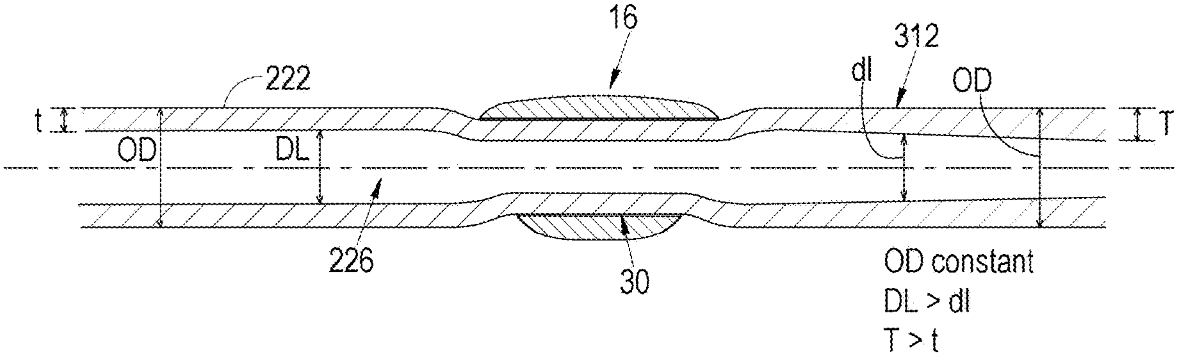
FIG. 34 shows a third embodiment of the elongate duct wherein the distal portion has a wall thickness which varies along the length of the distal portion, in accordance with an aspect of the present disclosure.

With reference to FIG. 34, a second example of the third embodiment of the elongate duct is designated by the reference numeral 312. The elongate duct has a distal portion 222 having a constant outer diameter and a wall thickness which varies along the length of the tube (from a relatively large wall thickness T to a relatively small wall thickness t). The outer diameter of the distal portion 122 is greater than the internal diameter of the internal passage 30 of the fixation body such that when the distal portion 122 is received in the internal passage 30, the wall of the distal portion deforms inwardly. The wall thickness of the distal portion tapers in thickness along at least along a portion of the length of the distal portion. The diameter of the lumen 226 tapers from a relatively larger diameter DL to a relatively smaller diameter dl. In use, the internal resistance to fluid flow through the distal portion can be adjusted by moving the position of the fixation body along the distal portion in order to provide for variations in patient aqueous fluid production rates. The elongate duct 212 is pinched by the fixation body 16 when it is received in the internal passage 30 of the fixation body, causing inward deformation of the duct in the region of the fixation body and thereby narrowing of the lumen.

In summary, a surgical method for treating glaucoma in a patient by lowering intraocular pressure in an eye of a patient, comprises:

providing the shunt 10 as defined and described hereinabove;

measuring the anatomical dimensions of the eye of the patient and a distance to a desired location for the formation of a bleb into which aqueous humor can drain, in order to determine an optimal length for the shunt;

sliding the fixation body 16, 116 along the distal portion 22 of the elongate duct 12 until a desired fixation body position is achieved corresponding to a desired length of the distal portion of the elongate duct and a desired position of the fixation body along the elongate duct for fixing the distal portion within the scleral channel;

cutting the distal portion of the elongate duct so as to adjust a length of the elongate duct;

opening the conjunctival/tenon's complex to create a pocket between the conjunctival/tenon's complex and the sclera;

using a surgical blade I, creating a passageway through scleral tissue so as to form a scleral channel from an external position at the pocket in the conjunctival/tenon's complex to the anterior/posterior chamber of the eye from which aqueous fluid is to be diverted;

inserting the distal portion of the elongate duct of the shunt into the scleral channel until the fixation body 16,116 lies within the scleral channel and the distal end 18.1 of the elongate duct lies within the anterior/posterior chamber of the eye; and closing the conjunctival/tenon's complex leaving the proximal end of the shunt lying within the pocket.

As may be recognized by those of ordinary skill in the art based on the teachings herein, numerous changes and modifications may be made to the above-described and other embodiments of the present disclosure without departing from the scope of the disclosure. The components of the shunt as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the shunt may include more or fewer components or features than the embodiments as described and illustrated herein. For example, the components and features of FIGS. 2-34 may be used interchangeably and in alternative combinations as would be modified or altered by one of skill in the art. Accordingly, this detailed description of the current embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. A shunt for treating glaucoma by lowering intraocular pressure in an eye of a patient, the shunt comprising:

an elongate duct defining a fluid passageway for diverting aqueous humor from a chamber of the eye, the elongate duct having a distal end and an opposite proximal end, the distal end being implantable in the chamber of the eye; and a fixation body extending outwardly from the elongate duct, the shunt being characterized in that:

the elongate duct has a distal portion defining the distal end of the duct, which is locatable in the scleral channel of the patient, the distal portion being deformable so as to permit the distal portion to conform to anatomical structures of the eye of the patient and being of a severable material in order to permit a surgeon to cut the distal portion to a desired length corresponding to a desired location for the formation of a bleb into which aqueous humor can drain; and a proximal portion, defining the proximal end of the elongate duct;

the distal portion has a distal lumen defining a distal part of the fluid passageway and the proximal portion has a proximal capillary lumen which is in fluid flow communication with the distal lumen, the proximal lumen having an internal diameter which is relatively smaller than an internal diameter of the distal lumen so as to reduce a flow rate of aqueous humor and regulate pressure along the proximal capillary lumen sufficient to prevent hypotony; and the fixation body of the shunt is slidably located on the distal portion of the elongate duct for fixing the distal portion of the duct within the scleral channel at a desired position determined by a required length of the shunt.

2. The shunt of claim 1, wherein the fixation body is frictionally located on the distal portion of the elongate duct in an arrangement wherein a coefficient of friction acting between the fixation body and the elongate duct is sufficient to adequately resist movement of the fixation body relative to the elongate duct when the elongate duct is implanted in the scleral channel of the patient yet permits sliding displacement of the fixation body relative to the elongate duct when a moderate force is applied to the fixation body by a surgeon.

3. The shunt of claim 1, wherein the fixation body defines an internal passage within which the elongate duct is received.

4. The shunt of claim 3, wherein the fixation body is located on the elongate duct in an interference fit wherein an internal diameter of the fixation body is slightly less than an external diameter of the distal portion of the elongate duct.

5. The shunt of claim 4, wherein the fixation body has an upper body portion configured for engagement with an upper side of the distal portion and a lower body portion configured for engagement with a lower side of the distal portion, the upper body portion being relatively wider than the lower body when viewed in side view, so as to cause bending of the elongate duct at regions thereof adjacent opposite proximal and distal sides of the fixation body when the distal portion of the elongate duct is received in the internal passage of the fixation body, thereby to resist displacement of the shunt within a scleral channel created within scleral tissue and direct the distal end away from the corneal endothelium and towards the iris plane of the patient.

6. The shunt of claim 4, wherein the fixation body defines a curved internal passage in which the elongate duct is received, the curvature of the internal passage being configured so as to cause bending of the elongate duct when the elongate duct is received therein, thereby to resist displacement of the shunt within a scleral channel created within scleral tissue and direct the distal end away from the corneal endothelium and towards the iris plane of the patient.

7. The shunt of claim 4, wherein, in order to facilitate adjustment of internal resistance to fluid flow through the proximal portion of the elongate duct, the proximal portion comprises an inner wall and an outer wall wherein the inner wall comprises a dissolvable substance which dissolves over a period of between 4 and 12 weeks.

8. The shunt of claim 4, wherein, in order to facilitate adjustment of internal resistance to fluid flow through the distal portion of the elongate duct, the distal portion has a wall thickness or diameter which varies along the length of the distal portion so that the internal flow resistance can be adjusted by sliding the fixation body along the distal portion.

9. The shunt of claim 1, wherein the shunt includes a scleral foot plate which is operatively connected to the proximal end of the elongate duct, for fixing the proximal end of the elongate duct to the sclera at the location of formation of the bleb and increasing the surface area for aqueous fluid drainage.

10. The shunt of claim 1, wherein the proximal portion of the elongate duct is releasably connected to the distal portion of the elongate duct.

11. The shunt of claim 1, wherein the proximal portion of the elongate duct is fixedly connected to the distal portion of elongate duct.

12. The shunt of claim 1, wherein the proximal portion of the elongate duct has a rigid construction.

13. The shunt of claim 1, wherein the proximal portion has an oval shape when viewed in cross section.

14. The shunt of claim 1, wherein the proximal portion has a curvature that conforms to that of an anatomical curvature of the ocular globe.

15. The shunt of claim 1, wherein the internal passage of the fixation body and an outer configuration of the distal portion of the elongate duct, are cylindrical.

16. The shunt of claim 1, wherein the fixation body has a pair of laterally-extending flanges which project outwardly from opposite sides thereof.

17. The shunt of claim 1, wherein the fixation body has a convexly rounded lower surface and a substantially flat upper surface.

18. The shunt of claim 1, wherein the fixation body is of a rigid construction.

19. The shunt of claim 1, wherein the chamber of the eye in which the shunt is implanted is the anterior chamber or the posterior chamber or the vitreous chamber of the eye.

20. The shunt of claim 1, wherein the shunt is configured to resist aqueous fluid flow at flow rates of between 1.5 to 3.0 micromillimetres per minute through the shunt using the Haigen Pouseille equation and a viscosity factor of 7.042 cP.

21. The shunt of claim 20, wherein the shunt is configured to resist aqueous fluid flow at flow rates of about 2 micromillimetres per minute through the shunt.

22. The shunt of claim 1, wherein the distal lumen has a diameter of between 0.12 mm and 0.3 mm.

23. The shunt of claim 22, wherein the distal lumen has a diameter of about 0.2 mm.

24. The shunt of claim 1, wherein the proximal capillary lumen has a diameter of between 0.035 mm and 0.06 mm.

25. The shunt of claim 24, wherein the diameter of the proximal capillary lumen is about 0.05 mm.

26. The shunt of claim 1, wherein the distal portion has a length of between 4 mm and 30 mm after cutting by the surgeon.

27. The shunt of claim 1, wherein the proximal portion has a length of between 1 mm and 8 mm.

28. The shunt of claim 27, wherein the proximal portion has a length of about 5 mm.

29. The shunt of claim 1, wherein the distal portion of the shunt is configured to resist fluid flow at a rate of 2.5 micromillimetres per minute.

30. The shunt of claim 1, wherein the distal portion of the elongate duct is configured to provide fluid flow resistance of less than 1 mmHg.

31. The shunt of claim 1, wherein the proximal capillary portion of the elongate duct is configured to provide fluid flow resistance of between 3 mmHg and 14 mmHg.

32. The shunt of claim 1, wherein an internal diameter of the distal lumen is relatively larger than an internal diameter of the proximal lumen in a ratio of between 2 and 8 times larger.

33. The shunt of claim 1, wherein a length of the distal portion is relatively longer than a length of the proximal portion in a ratio of between 2 and 30 times longer.

* * * * *